United States Patent
Nakatate et al.

(10) Patent No.: US 9,801,528 B2
(45) Date of Patent: Oct. 31, 2017

(54) GUIDEWIRE

(71) Applicant: FUJIKURA LTD., Tokyo (JP)

(72) Inventors: Kenichi Nakatate, Sakura (JP); Hitoe Ilkura, Sakura (JP)

(73) Assignee: FUJIKURA LTD., Koto-ku, Tokyo (JP)

( * ) Notice: Subject to any disclaimer, the term of this patent is extended or adjusted under 35 U.S.C. 154(b) by 122 days.

(21) Appl. No.: 14/779,088

(22) PCT Filed: Oct. 21, 2013

(86) PCT No.: PCT/JP2013/078454
§ 371 (c)(1),
(2) Date: Sep. 22, 2015

(87) PCT Pub. No.: WO2014/155794
PCT Pub. Date: Oct. 2, 2014

(65) Prior Publication Data
US 2016/0045101 A1    Feb. 18, 2016

(30) Foreign Application Priority Data

Mar. 25, 2013 (JP) .................................. 2013-062246

(51) Int. Cl.
*A61B 6/00* (2006.01)
*A61B 1/012* (2006.01)
(Continued)

(52) U.S. Cl.
CPC ........ *A61B 1/0125* (2013.01); *A61B 1/00078* (2013.01); *A61B 1/04* (2013.01);
(Continued)

(58) Field of Classification Search
CPC . A61B 5/6851; A61B 1/0125; A61B 1/00078; A61B 1/04; A61B 1/0684;
(Continued)

(56) References Cited

U.S. PATENT DOCUMENTS 5,514,128 A * 5/1996 Hillsman ............. A61B 18/245
 600/585
6,004,279 A 12/1999 Crowley et al.
(Continued)

FOREIGN PATENT DOCUMENTS

| EP | 2 621 158 A2 | 7/2013 |
| JP | 6-217931 A | 8/1994 |

(Continued)

OTHER PUBLICATIONS

International Search Report for PCT/JP2013/078454 dated Dec. 24, 2013 [PCT/ISA/210].
(Continued)

*Primary Examiner* — Robert N Wieland
(74) *Attorney, Agent, or Firm* — Sughrue Mion, PLLC

(57) ABSTRACT

[Problem] To provide a guidewire that has good operability and that can perform procedures efficiently.
[Solution to Problem] A guidewire is for guiding insertion of a medical appliance into a subject. The guidewire includes an inserting portion and an observation optical system. The inserting portion has a first part and a second part that has higher flexibility than the first part, and the inserting portion is to be inserted into the subject. The observation optical system is provided to the inserting portion, and the observation optical system is provided for observing inside the subject.

10 Claims, 8 Drawing Sheets

(51) Int. Cl.
*A61B 1/00* (2006.01)
*A61B 1/04* (2006.01)
*A61B 1/06* (2006.01)
*A61B 1/07* (2006.01)
*A61B 5/00* (2006.01)
*A61M 25/09* (2006.01)

(52) U.S. Cl.
CPC .............. *A61B 1/0684* (2013.01); *A61B 1/07* (2013.01); *A61B 5/6851* (2013.01); *A61M 25/09* (2013.01); *A61M 2025/09058* (2013.01); *A61M 2025/09183* (2013.01)

(58) Field of Classification Search
CPC .............. A61B 1/07; A61B 2090/306; A61B 2090/3614; A61B 17/8819; A61B 8/12
See application file for complete search history.

(56) References Cited

U.S. PATENT DOCUMENTS

| | | | |
|---|---|---|---|
| 6,485,413 B1* | 11/2002 | Boppart | A61B 1/00096 356/450 |
| 2003/0191379 A1 | 10/2003 | Benaron et al. | |
| 2004/0034311 A1 | 2/2004 | Mihalcik | |
| 2006/0149129 A1 | 7/2006 | Watts et al. | |
| 2006/0241768 A1* | 10/2006 | Trieu | A61F 2/441 623/17.12 |
| 2007/0016055 A1 | 1/2007 | Cao et al. | |
| 2011/0063428 A1 | 3/2011 | Sonnenschein et al. | |
| 2012/0078055 A1* | 3/2012 | Berci | A61B 1/0005 600/188 |
| 2012/0116156 A1* | 5/2012 | Lederman | A61B 1/05 600/109 |
| 2015/0190113 A1* | 7/2015 | Vardi | A61B 5/0095 600/463 |

FOREIGN PATENT DOCUMENTS

| | | |
|---|---|---|
| JP | 7-275366 A | 10/1995 |
| JP | 9-24019 A | 1/1997 |
| JP | 2000-503225 A | 3/2000 |
| JP | 2003-534056 A | 11/2003 |
| JP | 2005-522256 A | 7/2005 |
| JP | 2008-526360 A | 7/2008 |
| JP | 2008-535630 A | 9/2008 |
| JP | 2009-500082 A | 1/2009 |
| JP | 2009-72431 A | 4/2009 |
| JP | 2013-504400 A | 2/2013 |
| WO | 97/25914 A1 | 7/1997 |
| WO | 2006/073725 A1 | 7/2006 |
| WO | 2006/110666 A2 | 10/2006 |

OTHER PUBLICATIONS

International Preliminary Report on Patentability dated Oct. 8, 2015 issued in counterpart application No. PCT/JP2013/078454.

* cited by examiner

GUIDEWIRE

CROSS REFERENCE TO RELATED APPLICATIONS

This application is a National Stage of International Application No. PCT/JP2013/078454, filed on Oct. 21, 2013, which claims priority from Japanese Patent Application No. 2013-062246, filed on Mar. 25, 2013, the contents of all of which are incorporated herein by reference in their entirety.

TECHNICAL FIELD

The present invention relates to guidewires.

BACKGROUND

An endoscope is a medical device that is used to observe within a subject. Due to miniaturization and increase in performance of solid-state image pickup devices (CCD sensor, CMOS sensor, and the like), endoscopes (namely, electronic endoscopes) that have been mounted with a solid-state image pickup device at the tip of an inserting portion are widely available.

As such an electronic endoscope, there are devices that are for observing inside a thin lumen such as a blood vessel, a bile duct, and a ureter. These endoscopes require complicated operations during insertion into the lumens. Thus, for example, there is a case where a guidewire is inserted in advance into a subject using fluoroscopy, and the endoscope is inserted along such guidewire. Note that, the guidewire is used to guide a medical appliance such as a catheter or a stent, other than the endoscope, to a target region within the subject.

CITATION LIST

Patent Literature

PTL 1 Japanese Patent Application Laid-open Publication No. 7-275366

SUMMARY

Technical Problem

However, even in the case of inserting a guidewire inside a thin lumen such as a blood vessel, a bile duct, and a ureter, complicated operations become necessary, as with the endoscope. Further, there arises a problem that by performing insertion of the guidewire and insertion of the endoscope separately, the procedure takes time and effort.

The present invention has been considered to solve the above-described problems, and an objective is to provide a guidewire that has good operability and that can perform procedures efficiently.

Solution to Problem

According to an aspect of the invention, a guidewire is for guiding insertion of a medical appliance into a subject. The guidewire includes an inserting portion and an observation optical system. The inserting portion has a first part and a second part that has higher flexibility than the first part, and the inserting portion is to be inserted into the subject. The observation optical system is provided to the inserting portion and the observation optical system is provided for observing inside the subject. Other features of this invention will be made clear from the description of this specification and the attached drawings.

Advantageous Effects of Invention

A guidewire according to this invention has good operability and can perform procedures efficiently.

DESCRIPTION OF EMBODIMENTS

Summary of Disclosure

Figure 1:
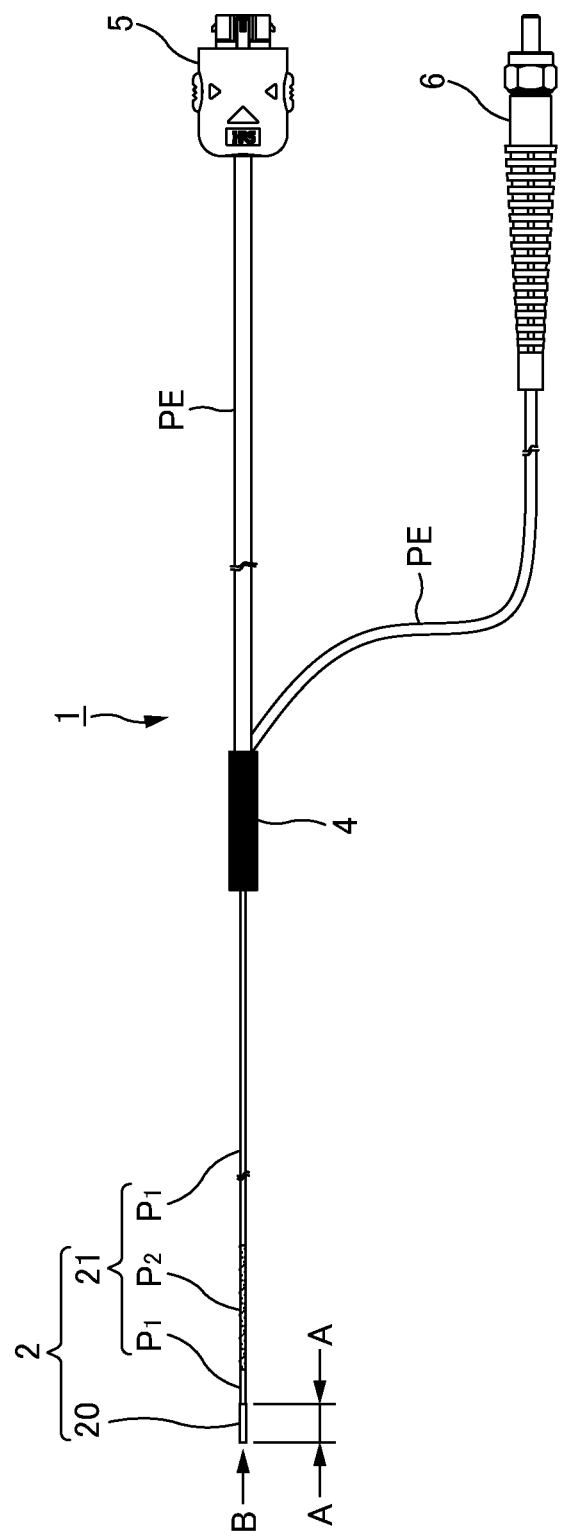
FIG. 1 shows a guidewire in an embodiment mode.

According to the description of this specification and the attached drawings, at least the following matters will become clear.

In other words, a guidewire will become clear that is for guiding insertion of a medical appliance into a subject, including:

an inserting portion to be inserted into the subject, the inserting portion having a first part and a second part that has higher flexibility than the first part; and
an observation optical system that is for observing inside the subject, the observation optical system being provided to the inserting portion.

Such a guidewire has good operability and can efficiently perform procedures.

Further, a guidewire will become clear, wherein
the inserting portion has
a tip portion configuring a tip and
a long shaft portion having the first part and the second part, the shaft portion being connected to the tip portion, and
the second part is provided to the tip portion side, in the shaft portion.

Such a guidewire can have bendability near the tip portion, thus having more operability.

Further, a guidewire will become clear, wherein
equal to or more than two slits are formed in at least a portion of a periphery of the second part.

Such a guidewire has good operability with a simple structure of merely providing the slits.

Further, a guidewire will become clear, wherein
a hydrophilic coating layer is formed in a periphery of the slits.

Such a guidewire can be easily inserted and/or removed to/from inside a subject.

Further, a guidewire will become clear, wherein
the observation optical system is configured including
an image pickup device that captures an image inside the subject, the image pickup device being provided to a tip of the inserting portion,
an objective lens provided in front of an imaging area of the image pickup device, and
an illuminating optical system that is for illuminating inside the subject.

Further, a guidewire will become clear, wherein
the observation optical system is configured including
an image guide fiber that transmits an optical image inside the subject,
an objective lens provided in front of an incidence plane of the image guide fiber,
an image pickup device that captures an optical image that has been transmitted from the image guide fiber, the image pickup device being provided to a rear end of the inserting portion, and
an illuminating optical system that is for illuminating inside the subject.

By providing such an observation optical system, other observation devices (such as an endoscope) do not need to be used. Thus, procedures can be efficiently performed.

Further, a guidewire will become clear, wherein
the image pickup device is a CMOS sensor.

By using the CMOS sensor as the image pickup device, miniaturization of the tip of the inserting portion becomes possible.

Further, a guidewire will become clear, wherein
the illuminating optical system includes a light guide fiber that guides light from a light source into the subject.

Further, a guidewire will become clear, wherein
a plurality of the light guide fibers are provided, and the plurality of the light guide fibers are arranged in a peripheral edge of the objective lens.

By arranging the light guide fibers in this way, the effect of halation can be reduced.

Further, a guidewire will become clear, wherein
the illuminating optical system is provided to a tip of the inserting portion and the illuminating optical system includes an LED light source that irradiates light to inside the subject.

By using such an illuminating optical system, the inserting portion can be made thinner in diameter.

Embodiment Mode

Figure 2:
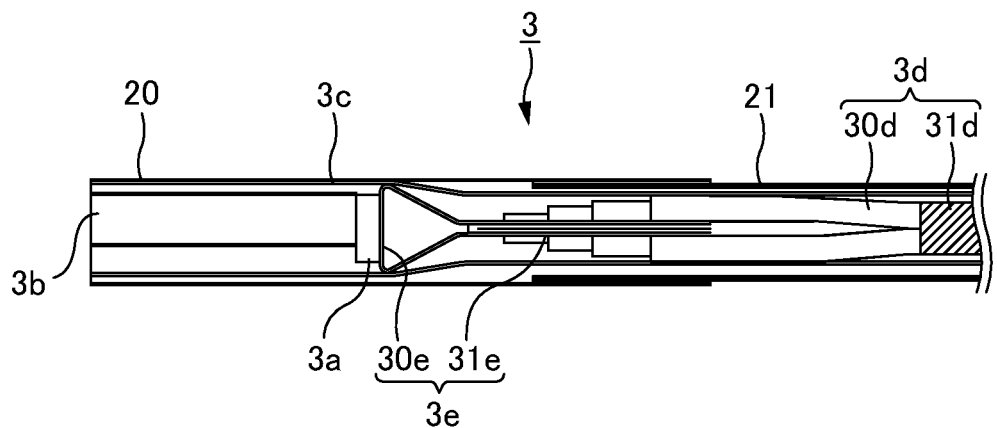
FIG. 2 shows the guidewire in the embodiment mode.
Figure 3:
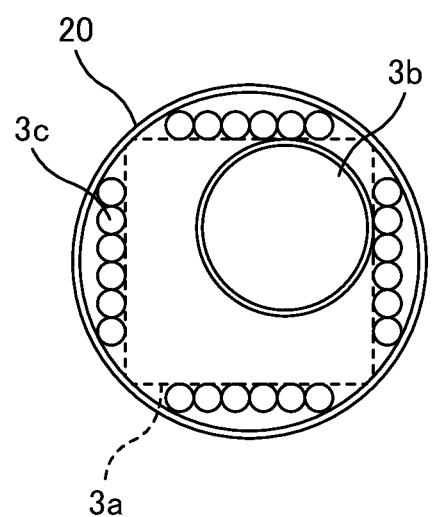
FIG. 3 shows the guidewire in the embodiment mode.

With reference to FIG. 1 to FIG. 4E, the configuration of a guidewire 1 according to the embodiment mode is described. FIG. 1 is an external view showing the entire guidewire 1. FIG. 2 is an A-A sectional view in FIG. 1. FIG. 3 is a view of the guidewire 1 seen from a B direction in FIG. 1. FIG. 4A to FIG. 4E are external views of a second part P2 (to be described later).

The guidewire 1 is for guiding insertion of a medical appliance (for example, a catheter, a stent, and the like) into a subject. The guidewire 1 is configured including an inserting portion 2, an observation optical system 3, a grip portion 4, a connector 5, and a plug 6 (refer to FIG. 1 to FIG. 3). The guidewire 1 in the embodiment mode has at least the inserting portion 2 and the observation optical system 3.

The inserting portion 2 is a long member to be inserted into a subject. The inserting portion 2 has a first part P1 and a second part P2 that has higher flexibility than the first part P1.

The inserting portion 2 according to the embodiment mode is configured including a tip portion 20 and a shaft portion 21. The tip portion 20 is fixed to the shaft portion 21 with an adhesive and the like.

The tip portion 20 configures a tip of the inserting portion 2. The tip portion 20 is a cylindroid hard member. The tip portion 20 is formed from, for example, stainless steel (SUS 304 and the like). The diameter of the tip portion 20 is, for example, 1.2 mm.

The observation optical system 3 is arranged inside the tip portion 20. The observation optical system 3 is configured including an image pickup device 3a, an objective lens 3b, light guide fibers 3c as an illuminating optical system, a cable portion 3d, and a FPC substrate 3e (refer to FIG. 2 and FIG. 3). The observation optical system 3 is fixed inside the tip portion 20 with a resin adhesive and the like. The observation optical system 3 in this embodiment mode has at least the image pickup device 3a, the objective lens 3b, and the illuminating optical system (the light guide fibers 3c).

The image pickup device 3a is an element that captures an image inside a subject. As the image pickup device 3a, for example, a CMOS sensor or a CCD sensor can be used. The CMOS sensor is adequate for miniaturization of the tip portion 20 compared to the CCD sensor.

The objective lens 3b is provided in front of an imaging area of the image pickup device 3a inside the tip portion 20. The objective lens 3b is arranged so that one lens surface (a surface to an opposite side of the lens surface opposing the imaging area) becomes flush with a tip surface of the tip portion 20. The image pickup device 3a captures an image of the subject via the objective lens 3b. The objective lens 3b can use, for example, a GRIN lens. Alternatively, the objective lens 3b can be configured as a lens group that combines a plurality of lenses (glass, plastic, and the like). A viewing angle of the objective lens 3b is, for example, 95 to 120 degrees. Further, in this embodiment mode, the objective lens 3b is arranged in a biased position with respect to a center of the imaging area of the image pickup device 3a (refer to FIG. 3).

The light guide fibers 3c are long members that guide light from a light source (not shown). The light guide fibers 3c are arranged so that outgoing faces (tip surfaces from which light goes out) are flush with the tip surface of the tip portion 20. Thus, the light that has been guided by the light guide fibers 3c (illuminating light) is irradiated from the outgoing surface to inside a subject. Base end sides of the light guide fibers 3c are inserted into inside the shaft portion 21 and connected with the light source (not shown) via the plug 6. As the light guide fibers 3c, fibers made of a multicomponent glass or plastic may be used.

In the embodiment mode, a plurality of the light guide fibers 3c is provided as the illuminating optical system. Further, the plurality of the light guide fibers 3c is arranged in the peripheral edge of the objective lens 3b. By arranging the light guide fibers 3c in this way, the outgoing surfaces of the light guide fibers 3c are positioned around the lens surface of the objective lens 3b (refer to FIG. 3). In this case, halation due to the illuminating light can be decreased.

The cable portion 3d is a unit in which a plurality of signal lines 30d (only two lines are shown in FIG. 2) is covered with a covering 31d. The signal lines 30d are lines to transmit drive signals (and drive power) to drive the image pickup device 3a and imaging signals (signals in which an image that has been captured has been converted to electrical signals) from the image pickup device 3a. The tip of the cable portion 3d (signal line 30d) is connected to the FPC substrate 3e. The base end side of the cable portion 3d (signal lines 30d) is inserted into inside the shaft portion 21 and connected to a processor (not shown) via the connector 5. The processor (not shown) is a device to be arranged outside a subject. The processor (not shown) has a function to form an image by processing imaging signals and a function to supply drive power of the image pickup device 3a.

The FPC substrate 3e is used in an electrical connection between the image pickup device 3a and the processor (not shown). In the embodiment mode the FPC substrate 3e is configured including a mounting portion 30e and two rear portions 31e. The mounting portion 30e is a part in which the image pickup device 3a is connected to the FPC substrate 3e. The rear portion 31e is a part that extends from the mounting portion 30e rearwards (to the base end side of the tip portion 20), in the case where the FPC substrate 3e is bent at both sides of the mounting portion 30e. The rear portion 31e and the cable portion 3d (signal lines 30d) are connected, and accordingly the image pickup device 3a is electrically connected to the processor (not shown) via the cable portion 3d. Note that, as long as the image pickup device 3a and the processor (not shown) can be electrically connected, the shape of the FPC substrate 3e is not limited to the above example. Further, the image pickup device 3a and the cable portion 3d can be directly connected. In this case, the FPC substrate 3e is not necessary.

The shaft portion 21 is connected to the tip portion 20, and the shaft portion 21 is a long cylindroid member having a first part P1 and a second part P2 with a higher flexibility than the first part P1. The shaft portion 21 is formed from stainless steel (SUS304 and the like), NiTi, Ti, and the like. The diameter of the shaft portion 21 is, for example, 0.9 mm to 1.2 mm. In the embodiment mode, the diameter of the shaft portion 21 is formed to be thinner than the diameter of the tip portion 20. In this way, by connecting the hard tip portion 20 to the shaft portion 21 that has flexibility, the insertion of the guidewire 1 to the subject becomes easy.

The first part P1 configures parts other than the second part P2 of the shaft portion 21. The first part P1 has a lower flexibility than the second part P2. Thus, the first part P1 can transmit a force applied from the grip portion 4 to the second part P2 and the tip portion 20.

On the other hand, the second part P2 has a higher flexibility than the first part P1. Thus, the second part P2 can easily bend due to a force equal to or greater than a constant amount being applied via the first part P1. The second part P2 is provided in a predetermined length to the tip portion 20 side of the shaft portion 21. In the embodiment mode, in order to secure a connecting part between the tip portion 20 and the shaft portion 21, the second part P2 is provided in a position 5 mm to 50 mm from the tip portion 20 side. Note that, the position of the second portion P2 can be set to a desired value in consideration of the length of the shaft portion 21 and the like.

The second part P2 in the embodiment mode is configured by forming a plurality of slits S in the shaft portion 21. The slits S are formed by laser processing to an outer surface of the shaft portion 21, for example.

By forming the slits S, the second part P2 can have more flexibility than the first part P1. Further, by adjusting the width and the length of the slits S, the push characteristics during inserting of the guidewire 1 into the subject via the grip portion 4, and the torque transmission characteristics during rotating of the guidewire 1 via the grip portion 4 can be adjusted. Further, by merely providing the slits S, the inserting portion 2 can be made to bend. Therefore, a complicated configuration (for example, refer to the configuration of a curved portion of a general endoscope.) for bending does not have to be used, and the guidewire 1 can be simplified and made thin in diameter.

Here, examples of the shapes of the slits S are described with reference to FIG. 4A to FIG. 4E. Note that, the shape of the slits S is not limited to those shown below. In other words, the slits S may be configured such that the second part P2 can have more flexibility than at least the first part P1. Further, the slits S may be formed as equal to or more than two in at least a part of a periphery of the second part P2.

Figure 4A:
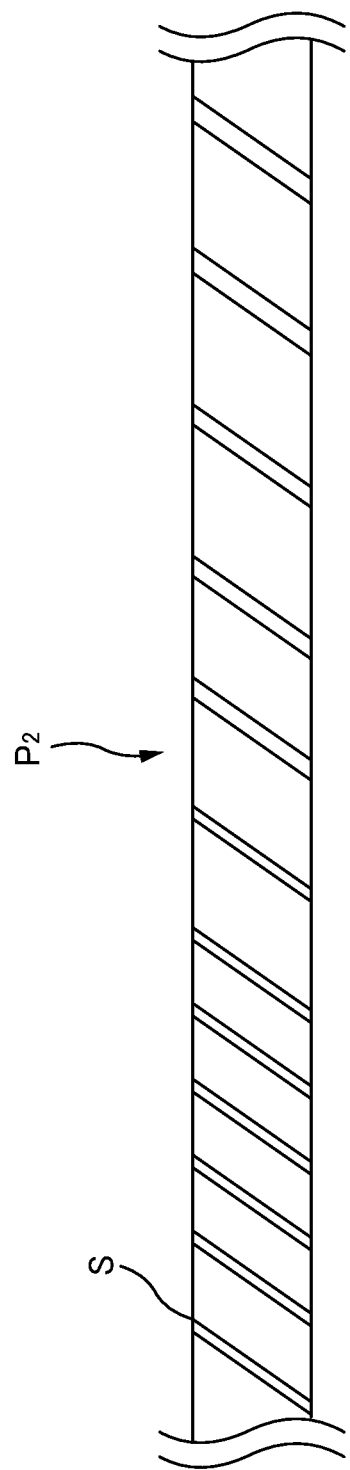
FIG. 4A shows a configuration of slits in the embodiment mode.

The slits S shown in FIG. 4A are configured by forming two parallel incisions helically in respect to a long axis direction of the inserting portion 2 (shaft portion 21). Such slits S may be configured merely by providing helical incisions in the periphery of the shaft portion 21, and thus the processing is easy.

Figure 4B:
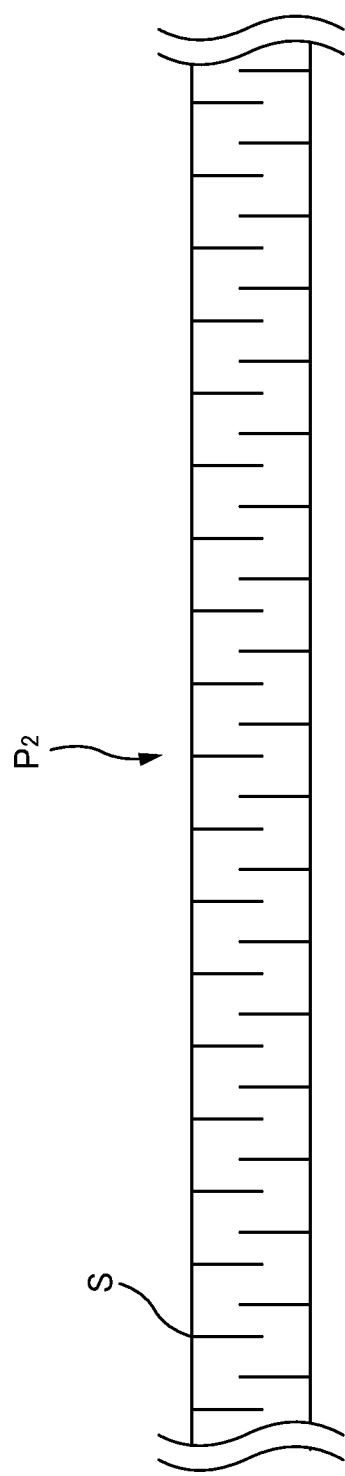
FIG. 4B shows a configuration of slits in the embodiment mode.

The slits S shown in FIG. 4B are configured by forming alternately the incisions (straight lines) in the short axis direction of the inserting portion 2 (shaft portion 21), with respect to the long axis direction. Such slits S may be configured merely by providing linear incisions in the periphery of the shaft portion 21, and thus the processing is easy.

Figure 4C:
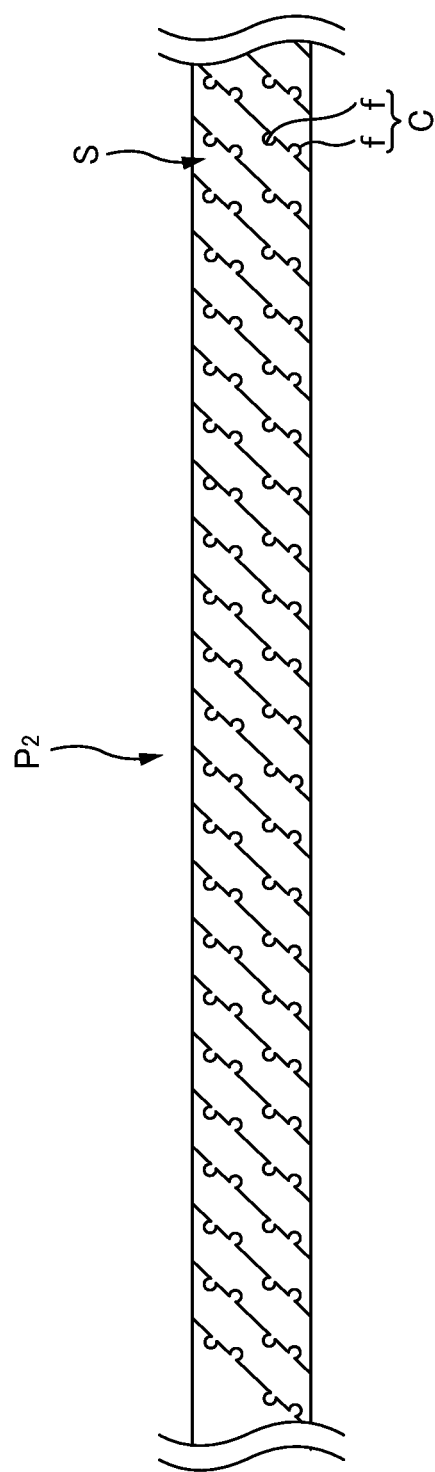
FIG. 4C shows a configuration of slits in the embodiment mode.

The slits S shown in FIG. 4C are configured by providing curved incisions C at predetermined intervals in the helical incision (however, one incision) as shown in FIG. 4A. Further, the incision part connecting the curved incisions C to each other is formed in a straight line. One curved incision C has two bending parts f. The two bending parts f are bent indifferent directions with respect to the helical incision. Such slits S can further increase flexibility of the second part P2.

Figure 4D:
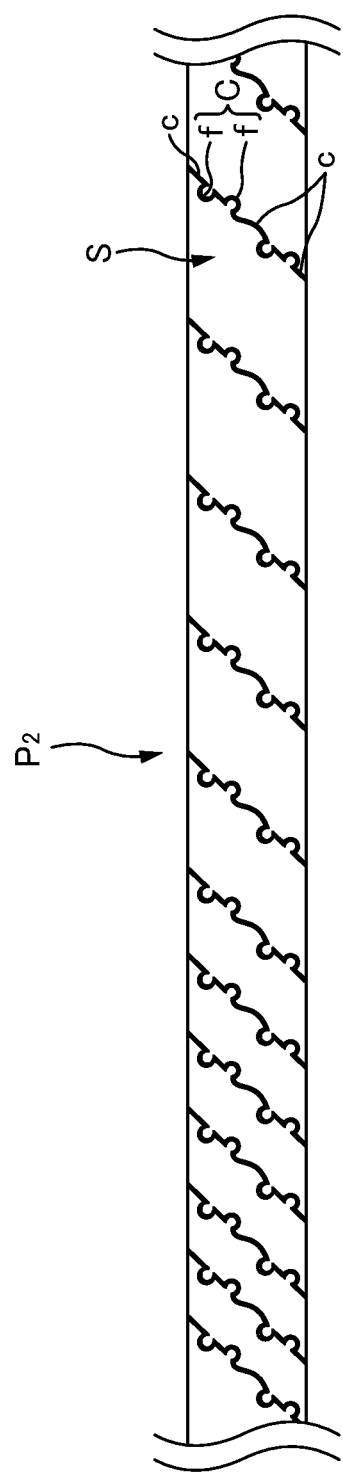
FIG. 4D shows a configuration of slits in the embodiment mode.

The slits S shown in FIG. 4D are configured by providing curved incisions C at predetermined intervals in the helical incision (however, one incision) as shown in FIG. 4A. Further, the incision part that connects the curved incisions C to each other is formed as a curve c with a smaller curvature than the curved incision C. Similar to FIG. 4C, the one curved incision C has two bending parts f. The two bending parts f are bent in different directions with respect to the helical incision. Such slits S further increase the flexibility of the second part P2, and the force applied in the case where the grip portion 4 is rotated can be easily transmitted. Thus, the push characteristics and the torque transmission characteristics of the inserting portion 2 can be increased.

Figure 4E:
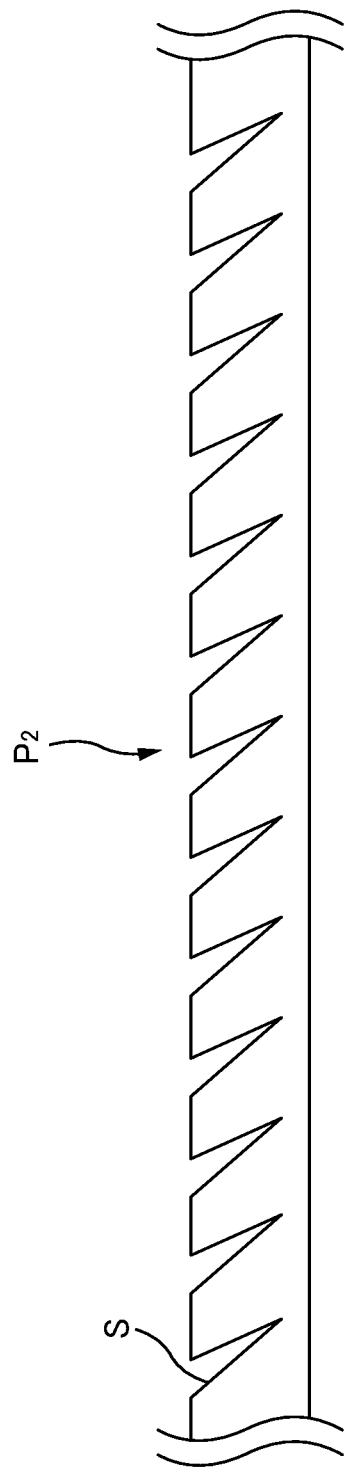
FIG. 4E shows a configuration of slits in the embodiment mode.

The slits S shown in FIG. 4E are configured by forming a plurality of notches in an inclined direction with respect to the long axis direction of the inserting portion 2 (shaft portion 21). The plurality of the notches is formed in the same side with respect to the long axis of the inserting portion 2 (for example, the upper side in FIG. 4E). Such slits S can make the second part P2 easily bend in a particular direction (a direction opposite to the direction of the notches).

Note that, a hydrophilic coating layer is preferably formed in the periphery of the slits S. Polymers to be used for the hydrophilic coating layer may be those that can provide hydrophilicity to the coating. In other words, the polymers may be synthetic polymers or biopolymers. The polymers may be a blend of both polymers or copolymers. Generally, hydrophilic polymers have a molecular weight in a range of approximately 8,000 to approximately 5,000,000 g/mol, preferably in a range of approximately 20,000 to approximately 3,000,000 g/mol, and more preferably in a range of approximately 200,000 to approximately 2,000,000 g/mol. As hydrophilic polymers, there are, for example, poly (lactum), polyvinyl pyrrolidone (PVP), polyurethane, acrylic acid and methacrylic acid homopolymer and copolymer, polyvinyl alcohol, polyvinyl ether, maleic anhydride copolymer, polyester, vinyl amine, polyethylene imine, polyethylene oxide, poly (carboxylic acid), polyamide, polyanhydride, polyphosphazene, cellulose, methylcellulose, carboxymethyl cellulose, hydroxymethyl cellulose, hydroxypropyl cellulose, heparin, dextran, polypeptide, collagen, fibrin, elastin, polysaccharide, chitosan, hyaluronic acid, alginate, gelatin, chitin, polylactide, polyglycol, polycaprolactone, albumin, oligopeptide, short-chain peptide, protein, oligonucleotide. By forming the hydrophilic coating layer, the outer surface of the second part P2 (inserting portion 2) can have lubricity. In other words, low friction characteristics can be obtained. Thus, inserting the guidewire 1 into the subject or drawing out of the guidewire 1 from the subject becomes easy.

The grip portion 4 is a part that is for gripping during operating (inserting or drawing out) the guidewire 1 from the subject. Doctors and others grasp the grip portion 4 with one hand, while pushing in with the other hand the inserting portion 2 to the subject. Alternatively, the doctors and others twist the grip portion 4, thus making the guidewire 1 (inserting portion 2) rotate inside the subject.

The connector 5 is a part that electrically connects a processor (not shown) and the guidewire 1. The cable portion 3d (signal lines 30d) from the grip portion 4 to the connector 5 is covered with a polyethylene tube PE, for example (refer to FIG. 1). The plug 6 is a part that optically connects a light source (not shown) and the guidewire 1 (the light guide fibers 3c). The light guide fibers 3c from the grip portion 4 to the plug 6 are covered with a polyethylene tube PE, for example (refer to FIG. 1).

Use Example of Guidewire 1

The guidewire 1 that has the above described configuration can be used in various parts of the subject. Note that, according to the part to be used, at least the length of the inserting portion 2 will differ.

For example, in the case of inserting a stent into an ureter, conventionally, a guidewire is inserted using radioscopy, and the stent is inserted along the guidewire. Then, an ureteroscope is inserted along the guidewire, and whether the stent has been arranged in the desired region (the affected area) is confirmed.

On the other hand, the guidewire 1 according to the embodiment mode has the observation optical system 3. Thus, the guidewire 1 can be easily inserted into the ureter while confirming an optical image. In other words, even in the case of inserting the guidewire 1 into the ureter, there is no need to perform it using radioscopy. Therefore, the guidewire 1 does not have to consider radiation amount during insertion. The guidewire 1 has the second part P2 that is high in flexibility in the inserting portion 2, thus the inserting operation into the ureter can be easily performed. The stent can be inserted along the guidewire 1 that has been inserted. In other words, the guidewire 1 according to the embodiment mode has the original function of the guidewire. Further, whether the stent has been arranged in the desired region can be confirmed with the guidewire 1. Therefore, there is no need to insert the ureteroscope to confirm the arrangement of the stent. Namely, the guidewire 1 according to the embodiment mode can save time and effort in the procedure. As a result thereof, it will lead to decrease of a patient's strain, and reduction of treatment (examination) costs.

Alternatively, it is also similar in the case of performing catheter treatment to the heart. Namely, the guidewire 1 can be easily inserted to the heart while confirming the optical image, and the radiation amount during insertion does not have to be considered. Further, the guidewire 1 has the second part P2 with a high flexibility in the inserting portion 2, thus the inserting movement to the heart can be easily performed. Further, in catheter treatment, a plurality of catheters need to be inserted into or drawn out the subject, and a plurality of catheters can be inserted into or drawn out along the inserted guidewire 1. In other words, the guidewire 1 according to the embodiment mode also has the function original to the guidewire. Further, the part in which catheter treatment is performed can be confirmed with the guidewire 1. Accordingly, there is no need to insert an angioscope to confirm the state of the treatment. In other words, the guidewire 1 according to the embodiment mode can save time and effort in the procedure. Further, as a result thereof, it will lead to decrease of a patient's strain, and reduction of treatment (examination) costs.

Manufacturing Method of Guidewire 1

An example of a manufacturing method of the above described guidewire 1 is described.

First, slits S are formed by laser processing to a part of the long shaft portion 21 with such as a processing device. The part that has been formed with the slits S functions as the second part P2.

Next, the manufacturer fixes the tip portion 20 and the tip side of the shaft portion 21 with an adhesive. In this way, the inserting portion 2 is completed.

Subsequently, the manufacturer inserts the image pickup device 3a and the light guide fibers 3c mounted to the FPC substrate 3e from the base end side of the shaft portion 21 (inserting portion 2). Then, the manufacturer adheres the image pickup device 3a (FPC substrate 3e), the light guide fibers 3c, and the objective lens 3b with respect to the tip portion 20 using resinous adhesive. In this way, the observation optical system 3 is fixed inside the tip portion 20. Note that, the FPC substrate 3e (rear portion 31e) is connected to the cable portion 3d (signal lines 30d).

Lastly, the manufacturer sets the grip portion 4 to the base end side of the shaft portion 21 (inserting portion 2), and provides the connector 5 to the base end of the cable portion 3d (signal lines 30d) extending from the grip portion 4. Further, the manufacturer provides the plug 6 to the base end of the light guide fibers 3c extending from the grip portion 4. In this way the guidewire 1 is completed.

Modified Example 1

In the above embodiment mode, the tip portion 20 and the shaft portion 21 are described as separate structures but it is not limited to this. For example, the observation optical system 3 may be arranged to the tip of the long member (inserting portion 2) with the same diameter, and a part (second part P2) with a higher flexibility than other parts (first part P1) may be provided to a part of the long member. In this case, the inserting portion 2 of the guidewire 1 can be made with one member. Accordingly, the tip portion 20 and the shaft portion 21 do not have to be adhered and manufacturing of the guidewire 1 can be simplified.

Modified Example 2

Figure 5:
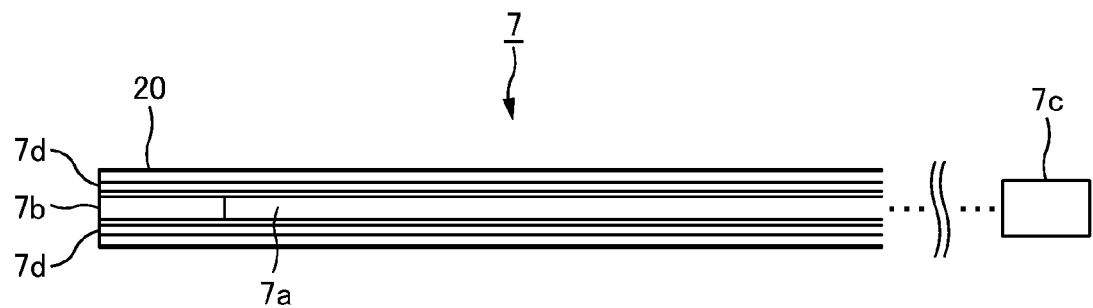
FIG. 5 shows a guidewire in a modified example 2.

Further, the observation optical system is not limited to the example of the above embodiment mode. FIG. 5 is a schematic diagram showing a cross-section of the tip portion 20 of the guidewire 1 in this modified example. An observation optical system 7 in this modified example is configured including an image guide fiber 7a, an objective lens 7b, an image pickup device 7c, and light guide fibers 7d as an illuminating optical system.

The image guide fiber 7a is inserted into inside the tip portion 20 and the shaft portion 21, and the optical image inside the subject is transmitted via the objective lens 7b. As the image guide fiber 7a, there can be used quartz fiber or plastic optical fiber (POF). The objective lens 7b is provided in front of the incidence plane of the image guide fiber 7a. The image pickup device 7c is provided to the rear end of the inserting portion 2, and captures the optical image transmitted from the image guide fiber 7a. The light guide fibers 7d guide light from the light source (not shown) to inside the subject. A plurality of the light guide fibers 7d are provided around the image guide fiber 7a.

By using the observation optical system 7, there is no need to provide the image pickup device to the tip of the inserting portion 2. Therefore, the tip (tip portion 20) of the inserting portion 2 can be miniaturized (made thin in diameter).

Modified Example 3

Figure 6:
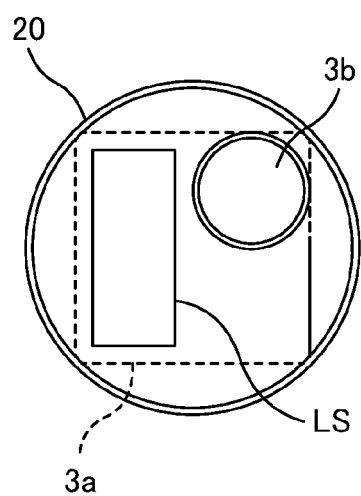
FIG. 6 shows a guidewire in a modified example 3.

Further, the illuminating optical system is not limited to the light guide fibers 3c. As the illuminating optical system, for example, an LED light source LS can also be used. The LED light source LS is provided inside the tip portion 20, and light is irradiated into the subject. FIG. 6 is a drawing showing a tip surface of the tip portion 20 of the guidewire 1. As shown in FIG. 6, in this modified example, the outgoing surface of the LED light source LS is arranged near the objective lens 3b (the LED light source LS is provided inside the tip portion 20). The LED light source LS irradiates light due to drive power being supplied via the signal lines 30d. In this case, the light guide fibers 3c become unnecessary, thus the inserting portion 2 (shaft portion 21) can be made thinner in diameter. Further, the plug 6 for connecting the light source (not shown) and the guidewire 1 also becomes unnecessary, thus the structure of the guidewire 1 can be simplified.

Modified Example 4

In the second part P2, the slits S are not always necessary. For example, the second part P2 may be formed with a material (a material with high flexibility) having more bendability than the first part P1. Alternatively, the second part P2 may be formed with a material having bendability, and formed with the slits 2. Further, in the above embodiment modes, the example is described with the second part P2 in only place in the inserting portion S, but it is not limited as such. As long as rigidity can be ensured so that the inserting portion 2 can be inserted into the subject, a plurality of the second parts P2 can be provided to the inserting portion 2.

REFERENCE SIGNS LIST 1 guidewire
2 inserting portion
3 observation optical system
3a image pickup device
3b objective lens
3c light guide fiber(s)
3d cable portion
3e FPC substrate
4 grip portion
5 connector
6 plug
20 tip portion
21 shaft portion
30d signal line(s)
31d covering
30e mounting portion
31e rear portion
P1 first part
P2 second part

The invention claimed is:

1. A guidewire that is for guiding insertion of a medical appliance into a subject, comprising:
    an inserting portion to be inserted into the subject, the inserting portion having a first part and a second part that has higher flexibility than the first part; and
    an observation optical system that is for observing inside the subject, the observation optical system being provided to the inserting portion,
    a helical slit being formed in at least a part of the second part, the helical slit having two or more types of pitch widths,
    the slit being provided with curved incisions at predetermined intervals, the curved incisions each having bending parts.

2. A guidewire according to claim 1, wherein
the inserting portion has
a tip portion configuring a tip and
a long shaft portion having the first part and the second part, the shaft portion being connected to the tip portion, and
the second part is provided to the tip portion side, in the shaft portion.

3. A guidewire according to claim 1, wherein
a hydrophilic coating layer is formed in a periphery of the slits.

4. A guidewire according to claim 1, wherein
the observation optical system is configured including
an image pickup device that captures an image inside the subject, the image pickup device being provided to a tip of the inserting portion,
an objective lens provided in front of an imaging area of the image pickup device, and
an illuminating optical system that is for illuminating inside the subject.

5. A guidewire according to claim 1, wherein
the observation optical system is configured including
an image guide fiber that transmits an optical image inside the subject,
an objective lens provided in front of an incidence plane of the image guide fiber,
an image pickup device that captures an optical image that has been transmitted from the image guide fiber, the image pickup device being provided to a rear end of the inserting portion, and an illuminating optical system that is for illuminating inside the subject.

6. A guidewire according to claim 4, wherein the image pickup device is a CMOS sensor.

7. A guidewire according to claim 4, wherein the illuminating optical system includes a light guide fiber that guides light from a light source to inside the subject.

8. A guidewire according to claim 7, wherein a plurality of the light guide fibers are provided, and the plurality of the light guide fibers are arranged in a peripheral edge of the objective lens.

9. A guidewire according to claim 4, wherein the illuminating optical system is provided to a tip of the inserting portion and the illuminating optical system includes an LED light source that irradiates light to inside the subject.

10. A guidewire according to claim 1, wherein at least two of the bending parts are formed and the two bending parts are bent in different directions with respect to the slit.

* * * * *